US005910409A

United States Patent [19]
Bhattacharjee et al.

[11] Patent Number: 5,910,409
[45] Date of Patent: Jun. 8, 1999

[54] METHODS AND REAGENTS FOR DETECTING FUNGAL PATHOGENS IN A BIOLOGICAL SAMPLE

[75] Inventors: Jnanendra K. Bhattacharjee; Vasker Bhattacherjee, both of Oxford, Ohio

[73] Assignee: Miami University, Oxford, Ohio

[21] Appl. No.: 08/650,809

[22] Filed: May 20, 1996

[51] Int. Cl.⁶ .............................. C12Q 1/68; C12P 19/34; C07H 21/04

[52] U.S. Cl. .......................... 435/6; 435/91.2; 435/91.1; 536/22.1; 536/24.3; 536/23.1; 935/77; 935/78

[58] Field of Search .................................. 536/22.1, 24.3, 536/23.1; 435/91.2, 6, 91.1; 935/77, 78

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,889,818 | 12/1989 | Gelfand et al. | 435/194 |
| 4,965,188 | 10/1990 | Mullis et al. | 435/6 |
| 5,075,216 | 12/1991 | Innis et al. | 435/6 |
| 5,079,352 | 1/1992 | Gelfand et al. | 536/27 |

OTHER PUBLICATIONS

Bodey and Fainstein, Systemic Candidiasis, p. 135 (Eds.) Raven Press, New York (1985).
Holmes, A.R. et al., Yeast–specific DNA probes and their application for the detection of Candida albicans, J. Med. Microbiol., 37:346–351 (1992).
Odds, F.C., In candida and candidosis, (Ed.) Leicester University Press, Leicester, United Kingdom (1989).
Musial, et al., Fungal Infections of the Immunocompromised Host: Clinical and Laboratory Aspects, Clin. Microbiol. Rev. 1:349–364 (1988).
Hopfer, R.L., et al., Detection and differentation of fungi in clinical specimens using polymerase chain reaction (PCR) amplification and resriction enzyme analysis, J. Med. Vet. Pharm. 31:65–75 (1993).
Buchman, T.G., et al., Detection of surgical pathogens by in vitro DNA amplification. Part I, Rapid identification of Candida albicans by in vitro amplification of a fungal specific gene. Surgery, 108:338–347 (1990).
Bhattacharjee, The –aminoadipate pathway for the Biosynthesis of Lysine in Lower Eukaryotes, CRC Critical rev. in Microbiol. 12:131–151 (1985).
Lejohn, Enzyme Regulation, Lysine Pathways and Cell Wall Structures as Indicators of Major Lines of Evolution in Fungi, Nature 231:164–168 (1971).
Vogel, Two Modes of Lysine Synthesis Among Lower Fungi: Evolutionary Significance, Biochim. Biophys. Acta 41:172–174 (1960).
Garrad and Bhattacharjee, Lysine biosynthesis in selected pathogenic fungi: Characterization of Lysine auxotrophs and the cloned LYS1 gene of Candida albicans, J. Bacteriol. 174:7379–7384 (1992).
Fujioka, Chemical mechanism of saccharopine dehydrogenase (NAD, L–lysine forming) as deduced from initial rate pH studies, Arch. Biochem. Biophys. 230:553–559 (1984).

Xuan, et al., Overlapping reading frames at the LYS5 locus in the yeast Yarrowia lipolytica, Mol. Cell. Biol. 10:4795–4806 (1990).
Goshorn, et al., Gene isolation by complementation in Candida albicans and applications to physical and gentic mapping, Infect. And Imm. 60:876–884 (1992).
Nucleic Acid Hybridization, (Eds.) Hames B.D. and Higgens, S.J., IRL Press, Oxford (1985).
R.H. Don, et al., 'Touchdown' PCR to circumvent spurious priming during gene amplification. Nucleic Acids Research, 19:4008 (1991).
R. Garrad, et al., Molecular and Functional Analysis of the LYS1 Gene of Candida albicans, Infec. and Imm., 62:11 5027–5031 (1994).
PCR Protocols; a Guide to Methods and Applications, (Eds.) M.A. Innis, D.H. Gelfand, J.J. Sninsky and T.J. White, Academic Press, Inc., New York (1990).
Ye, Z. Et al., Use of –aminoadipate and lysine as sole nitrogen source by Schizosaccharomyces pombe and selected pathogenic fungi, J. Basic Microbiol. 31 (1991) 2, 149–156.
Kan, V.L., Polymerase Chain Reaction for the Diagnosis of Candidemia, The Journal of Infectious Diseases 1993:168:779–83.
Ford, R.A, et al., Physical and functional characterization of the cloned lsyl+ gene of Schizosaccharomyces pombe, J. Basic Microbiol. 33 (1993) 3, 179–186.
Check, William, Molecular Techniques Shed Light on Fungal Genetics: Genetic analyses are leading researchers to reclassify fungi and better understand fungal pathogens, ASM News, vol. 60, No. 11, 1994, pp. 593–596.
Charles, I.G. et al, Molecular cloning and characterization of protective outer membrane protein P.69 from Bordetella pertussis, Proc. Natl. Acad. Sci. USA, vol. 86, pp. 3554–3558, May 1989.
The Evolution of Metabolic Function, (Ed.) Mortlock, Robert P., CRC Press, New York, 1992.
DNA Fingerprinting: State of the Science, (Eds.) Pena, S.D.J., Chakraboty, R., Epplen, J.T., Jeffreys, A.J., Birkhauser Verlag basel, Switzerland, 1993.
Ruchel, R., Diagnosis of invasive mycoses in severly immunosuppressed patients, Ann Hematol (1993) 67:1–9.
Cheung, L.L. et al., Development of DNA Probes for Candida albicans, Diagn Microbil Infect Dis, 1988:10:171–179.

*Primary Examiner*—Stephanie W. Zitomer
*Assistant Examiner*—Joyce Tung
*Attorney, Agent, or Firm*—McDonnell, Boehnen, Hulbert & Berghoff

[57] ABSTRACT

The present invention provides materials and methods for sensitively and selectively screening biological samples for the presence of Candida albicans, a fungal pathogen of increasing clinical concern. Specifically, nucleic acids, reagents, and primers for DNA amplification are provided that will allow amplification of a 526 base pair oligonucleotide from DNA containing Candida albicans. Methods for using such primers in DNA amplification are also provided.

24 Claims, 4 Drawing Sheets

TTAACAAAGAGAGATTGTTTAAGATTACAAAGTTTAGCTGAAAATGTGTTTATTG

TTAACATGCTATGGTCACTACTGCAAACACAGAGATCAGTGTCATACT

TTGAAATCAAAAGTCGTAAAGCAGATCCTACATACTTAAAAAACTTGA

AAGCTGTGATGCCTGCAGGGACCGGTATGCACAACGTTCAATTGTTA

GTCGTTAATAGAAATGACCGCTCGCAAACCTGTGGTGTTGGGGAAGT

TGGTGAAATCTATGTTAGGGCAGCTGGTTTAGCCGAAGGATACCGTG

GATTGCCTGATTTAAATGCTGCTAAGTTTATTACCAATTGGTATGTCAA

CCCAGACAAATGGATCGAACAAGATGAAGCTAACAAAAAATCCAGTG

AAACGCTGGAGAGAACATGGCTGGTTAAACCAAGAGACAGAATGTATAG

ATCTGGTGATTTGGGTCGTTATTTCCTGGATGGTAATGTTGAATGTTGTGGTAG

AGCAGATGACCAAGTCAAGATTAGAGGTTTCAGAA

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
           (A) LENGTH: 27 base pairs
           (B) TYPE: nucleic acid
           (C) STRANDEDNESS: single
           (D) TOPOLOGY: linear (iii) HYPOTHETICAL: NO (vi) ORIGINAL SOURCE:
           (A) ORGANISM: Candida Albicans (xi) SEQUENCE DESCRIPTION: SEQ ID NO:1:

AACAAGCTTA ACAAAGAGAG ATTGTTT                                27

(2) INFORMATION FOR SEQ ID NO:2:

(i) SEQUENCE CHARACTERISTICS:
           (A) LENGTH: 26 base pairs
           (B) TYPE: nucleic acid
           (C) STRANDEDNESS: single
           (D) TOPOLOGY: linear (iii) HYPOTHETICAL: NO (vi) ORIGINAL SOURCE:
           (A) ORGANISM: Candida Albicans (xi) SEQUENCE DESCRIPTION: SEQ ID NO:2:

AACAAGCTTC TGAAACCTCT AATCTT                                 26

(2) INFORMATION FOR SEQ ID NO:3:

(i) SEQUENCE CHARACTERISTICS:
           (A) LENGTH: 27 base pairs
           (B) TYPE: nucleic acid
           (C) STRANDEDNESS: single
           (D) TOPOLOGY: linear (iii) HYPOTHETICAL: NO (vi) ORIGINAL SOURCE:
           (A) ORGANISM: Saccharomyces cerevisiae (ix) FEATURE:
           (D) OTHER INFORMATION: N represents G or A (xi) SEQUENCE DESCRIPTION: SEQ ID NO:3:

AACAAGCTTN ACNAAACGTG ATTGTCT                                27

(2) INFORMATION FOR SEQ ID NO:4:

(i) SEQUENCE CHARACTERISTICS:
           (A) LENGTH: 26 base pairs
           (B) TYPE: nucleic acid
           (C) STRANDEDNESS: single
           (D) TOPOLOGY: linear (iii) HYPOTHETICAL: NO (vi) ORIGINAL SOURCE:
           (A) ORGANISM: Saccharomyces cerevisiae (ix) FEATURE:
           (D) OTHER INFORMATION:  First N represents G or T and second N represents C or A (xi) SEQUENCE DESCRIPTION: SEQ ID NO:4:

| AACAAGCTTC NGAANCCACG AATTTT | 26 |

(2) INFORMATION FOR SEQ ID NO:5:

(i) SEQUENCE CHARACTERISTICS:
      (A) LENGTH: 522 base pairs
      (B) TYPE: nucleic acid
      (C) STRANDEDNESS: single
      (D) TOPOLOGY: linear    (iii) HYPOTHETICAL: NO    (vi) ORIGINAL SOURCE:
      (A) ORGANISM: Saccharomyces cerevisiae    (xi) SEQUENCE DESCRIPTION: SEQ ID NO:5:

| TTAACAAAGA GAGATTGTTT AAGATTACAA AGTTTAGCTG AAATGTGTTA | 50 |
| TTGTTAACAT GCTATGGTCA CTACTGCAAA CACAGAGATC AGTGTCATAC | 100 |
| TTTGAAATCA AAAGTCGTAA AGCAGATCCT ACATACTTAA AAAACTTGAA | 150 |
| AGCTGTATGC CTGCAGGGAC CGGTATGCAC AACGTTCAAT TGTTAGTCGT | 200 |
| TAATAGAAAT GACCGCTCGC AAACCTGTTG GTGTTGGGAA GTTGGTGAAA | 250 |
| TCTATGTTAG GGCAGCTGGT TTAGCCAAGG ATACCGTGGA TTGCCTGATT | 300 |
| TAAATGCTGC TAAGTTTATT ACCAATTGGT ATGTCAACCC AGACAAATGG | 350 |
| ATCGAACAAG ATGAAGCTAA CAAAAAATCC AGTGAAACGC TGGAGAGAAC | 400 |
| ATGGCTGGTT AAACCAAGAG ACAGAATGTA TAGATCTGGT GATTTGGGTC | 450 |
| GTTATTTCCT GGATGGTAAT GTTGAATGTT GTGGTAGAGC AGATGACCAA | 500 |
| GTCAAGATTA GAGGTTTCAG AA | 522 |

METHODS AND REAGENTS FOR DETECTING FUNGAL PATHOGENS IN A BIOLOGICAL SAMPLE

BACKGROUND OF THE INVENTION

1. Field of the Invention

The present invention relates to novel methods for identifying fungal pathogens in a biological sample. In particular, this invention relates to methods for screening biological samples for the presence of *Candida albicans* that employ novel DNA amplification primers.

2. Background of the Invention

*Candida albicans*, once considered a relatively minor fungal pathogen, has recently become a particularly serious health concern as the causative agent of candidosis (also called candidiasis). The incidence of *C. albicans* infections is rising rapidly with the increase in immune deficiency diseases and immunosuppressive therapy (Bodey and Fainstein, In Systemic Candidiasis, pp. 135 (Eds., Raven Press, New York 1985). Candidosis is a common nosocomial infection afflicting both immunosuppressed and post-operative patients. (Holmes, A. R., et al. Yeast-specific DNA probes and their application for the detection of *Candida albicans*, J. Med. Microbiol., 37:346–351 (1992)). Although candidosis is a particular concern among immunocompromised individuals, Candida infections are not limited to this group. *C. albicans* is the major opportunistic fungal pathogen in humans (Odds, F. C., In Candida and candidosis, (Ed.) Leicester University Press, Leicester, United Kingdom (1989)) and is capable of establishing infection whenever the host immune system or normal flora are perturbed.

Although the *C. albicans* species is a particular health concern, other species of the Candida genus are also pathogenic. The genus Candida is comprised of approximately 200 diverse yeast species classified together due to their lack of a sexual cycle (Meyer et al., In Genus 4, Candida, pp. 1–12, (Ed.) N. J. W. Kreger-van Riij, Elsevier, Amsterdam (1984)). A minority of Candida species are pathogenic and 80% of the clinical isolates are either *C. albicans* or *C. tropicalis* (Hopfer, R. L. In Mycology of Candida Infections, G. P. Bodey, an V. Fainstein (eds.), Raven Press, New York (1985)).

In immunocompromised hosts, candidosis is a life threatening condition. The prognosis for a patient infected with *C. albicans* can be improved markedly, however, with prompt antifungal treatment. Treatment may be delayed until a positive diagnosis of Candidosis is obtained since antifungal drugs are toxic. See Holmes, et al., 1992.

Diagnostic tests for the identification of *C. albicans* or other fungal pathogens in vivo often require complete cultural identification protocols (Musial et al., Fungal Infections of the Immunocompromised Host: Clinical and Laboratory Aspects, Clin. Microbiol. Rev. 1:349–364 (1988)). Methods currently used for the diagnosis of fungal pathogens include: cultural identification, biopsy, serodiagnosis, identification of metabolites, isoenzyme determination, pulsed field gel electrophoresis and analysis of restriction fragment length polymorphisms. Most of these methods are time consuming, laborious and provide inconclusive results. Serodiagnosis is particularly unacceptable for the identification of candidosis, as most individuals have been exposed to Candida and therefore have circulating antibodies against Candida even in the absence of infection. Thus, serodiagnosis can only be accomplished by determining a rise in the titer for anti-Candida antibodies as compared to the titer present in the non-disease state. Such titers are generally unavailable, rendering the technique of serodiagnosis less attractive for the diagnosis of Candida infection.

Potential methods for diagnosing fungal infections through DNA screening have focused on detecting specific nucleotide sequences such as ribosomal DNA (Hopfer, R. L. et al., Detection and differentiation of fungi in clinical specimens using polymerase chain reaction (PCR) amplification and restriction enzyme analysis, J. Med. Vet. Pharm. 31:65–75 (1993)) and the cytochrome $P_{450}$ genes (Buchman, T. G. et al., Detection of surgical pathogens by in vitro DNA amplification. Part I, Rapid identification of *Candida albicans* by in vitro amplification of a fungal specific gene. Surgery, 108:338–347 (1990)). However, no commercial diagnostic techniques embodying methods related to the identification of these genes in biological samples are known.

One impediment to developing nucleic acid based screening techniques for Candidosis is that basic information about uniquely fungal metabolic pathways and cognate genes of *C. albicans* is lacking (Kurtz et al., Molecular Genetics of *Candida Albicans*, pp. 21–73, Kirsch, Kelly and Kurtz (eds.) CRC Press Inc. Boca Raton, Fla. (1990)). The sequences of over 330 *C. albicans* genes are available in computerized databases, and very few are involved in amino acid biosynthesis. The relatively small database of genetic information available for *C. albicans* places limitations upon the number of DNA sequences that can be used as targets for screening probes and concomitantly reduces the likelihood of identifying a sequence unique to fungi and amenable to identification through DNA screening techniques. For example, very few of these genes are involved in amino acid biosynthesis.

Among the proteins that have been studied in *C. albicans* and other pathogenic fungi are the enzymes that make up the α-aminoadipate pathway for the biosynthesis of lysine. This unique pathway has been identified in Phycomycetes, Euglenids, yeasts and other higher fungi (Bhattacharjee, The α-aminoadipate Pathway for the Biosynthesis of Lysine in Lower Eukaryotes, CRC Critical Rev. in Microbiol. 12:131–151 (1985); Lejohn, Enzyme Regulation, Lysine Pathways and Cell Wall Structures as Indicators of Evolution in Fungi, Nature 231:164–168 (1971); and Vogel, Two Modes of Lysine Synthesis Among Lower Fungi: Evolutionary Significance, Biochim. Biophys. Acta 41:172–174 (1960)) and is present in *C. albicans* and other pathogenic fungi (Garrad, R. Masters Thesis, Miami University (1989) and, Garrad and Bhattacharjee, Lysine biosynthesis in selected pathogenic fungi: Characterization of lysine auxotrophs and the cloned LYS1 gene of *Candida albicans*, J. Bacteriol. 174:7379–7384 (1992)). Lysine is an essential amino acid for humans and animals and is synthesized by the diaminopimelic acid pathway in bacteria and plants. The α-aminoadipate pathway consists of eight enzyme catalyzed steps; there appear to be seven free intermediates in *S. cerevisiae* (Bhattacharjee, The α-aminoadipate pathway for the biosynthesis of lysine in lower eukaryotes, CRC Critical Review in Microbiol. 12:131–151 (1985)).

SUMMARY OF THE INVENTION

An object of this invention is to provide an improved method of identifying the presence of *Candida albicans* in a biological sample. Another object of the present invention is to provide improved materials and reagents for use in screening biological samples for the presence of *C. albicans*.

The invention herein achieves this object by providing novel nucleic acids, reagents and PCR primers capable of selectively amplifying a unique fungal nucleic acid from genomic DNA derived from *Candida albicans*. The present invention provides PCR primers capable of sensitively and selectively amplifying a 526 base pair sequence from DNA present in the genome of *Candida albicans*. The invention also encompasses the individual nucleic acids that comprise the inventive primers. Reagents comprising the inventive nucleic acids are also a part of the invention. Further, methods for using the inventive nucleic acids, primers and reagents are provided wherein such nucleic acids, primers and reagents are used to screen a biological sample for the presence of a 526 base pair DNA sequence that is unique to *Candida albicans*.

The nucleic acids, primers, reagents and methods of the present invention represent improved materials and methods for screening biological samples for the presence of *Candida albicans*.

DETAILED DESCRIPTION OF INVENTION

This invention provides methods and reagents for sensitively and specifically detecting the presence of *Candida albicans* in biological samples. In the inventive method, a biological sample may be screened to determine whether or not the sample contains *Candida albicans*; the screening is carried out through DNA amplification using specifically designed DNA replication primers (this process is commonly referred to as the polymerase chain reaction, or PCR). The inventive primers (and reagents comprising such primers) disclosed herein are used in the inventive methods to screen DNA contained in a biological sample for the presence of a 526 base pair sequence within the Candida genome that is unique to *C. albicans*. If this 526 base pair sequence is present in the screened biological sample at a copy number of 100 copies/ml (and possibly as low as 10 copies/ml), conducting PCR on DNA originating in such biological sample using the inventive primers will result in amplification of the 526 base pair oligonucleotide. Detection of the amplified oligonucleotide following PCR confirms the presence of *C. albicans* in the original biological sample.

Figure 1:
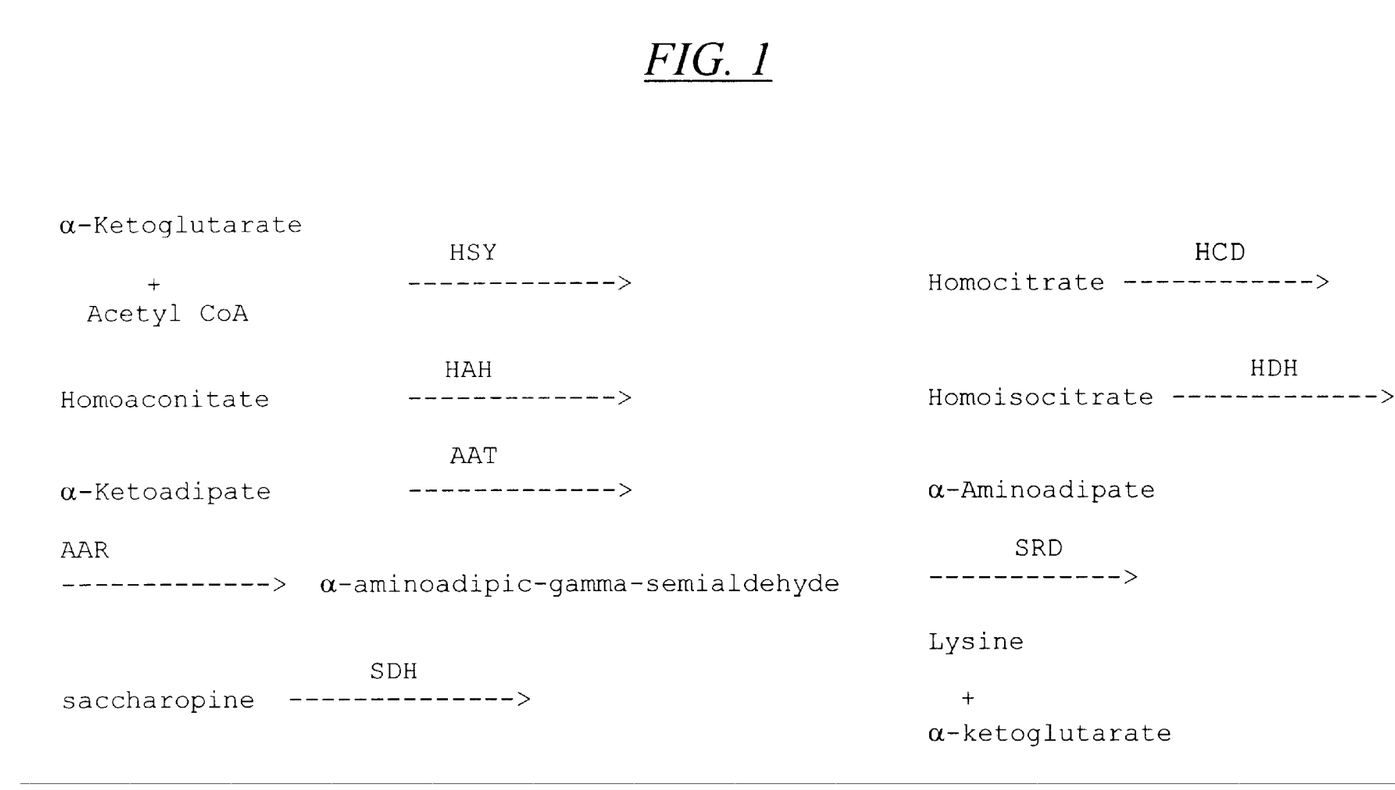
FIG. 1 schematically depicts the enzymatic pathway known as the α-aminoadipate pathway.

Over three hundred thirty genes of the *C. albicans* genome have been sequenced, but very few of the genes involved in amino acid biosynthesis had been sequenced prior to the current invention. The *C. albicans* LYS2 gene codes for the large subunit of aminoadipate reductase, one of the enzymes of the pathway used in fungi to generate lysine. This pathway is called the alpha aminoadipate pathway ("the a-AA pathway"); the enzymes and intermediates of this pathway are represented in FIG. 1. The LYS2 gene was originally cloned by Magee et al. (S. Scherer and P. T. Magee (1990) Genetics of *C. albicans, Microbial Reviews*, 54:226–241). The sequence of the LYS2 gene of *C. albicans*, determined by Suvarna and Bhattacharjee (manuscript in preparation), and has been submitted to GenBank for assignment of an accession number.

Aminoadipate reductase is one enzyme of eight which make up the alpha aminoadipate pathway for the biosynthesis of the amino acid lysine. Because this pathway is thought to be specific to fungi and is not found in mammals, the genes coding for the enzymes of the pathway provide unique targets for use in screening biological samples for the presence of fungi. The inventive primers amplify the 526 base pair oligonucleotide from *C. albicans* because these primers were designed based on the sequence of the *C. albicans* gene for the large subunit of aminoadipate reductase. The inventive primers are both sensitive and specific for the presence of Candida, as shown by the Examples set forth below.

As used herein, the term "oligonucleotide" is defined as a molecule composed of two or more deoxyribonucleotides or ribonucleotides, but which does not comprise all of the codons necessary for the expression of a full protein. For the purposes of the present invention, an oligonucleotide is considered to include (but not be limited to) the 526 base pair amplification product of the present invention.

A nucleic acid that is "complementary" to a reference nucleic acid shall be defined as a nucleic acid that is the antisense of the reference nucleic acid. As indicated below, only the primers VB21 and VB22 have been found to be useful in the present invention. However, minor modifications to such primers may nevertheless allow amplification of the desired 526 base pair oligonucleotide, and therefore such closely related primers are also considered to be within the scope of the present invention.

A reagent, for the purposes of this disclosure, shall be defined as a composition of matter used in performing diagnostic or research procedures (particularly PCR) that incorporates at least one of the inventive primers. Such reagents also may comprise water and/or a buffer (especially Tris).

As used herein, a nucleic acid amplification kit shall be taken to mean a kit containing one or more components designed to be used in conducting PCR. In addition to at least one of the inventive PCR primers identified herein (which may be lyophilized or may optionally be provided dissolved in a solvent containing such components as water, Tris, or other components known to those of ordinary skill in the art) such kits may optionally include the following: a buffer (full strength or concentrated), which may contain Tris, DMSO and/or other additives; Taq enzyme (or similar thermostable DNA polymerase used by those of skill in the art in conducting PCR), preferably in solution, such solution containing glycerol and/or water; magnesium chloride; and dATP, dCTP, dGTP and dTTP. The contents of such PCR kits and the foregoing compositions may be modified by those of ordinary skill in the art to achieve specific results and such kits and compositions are intended to be part of the present invention.

Reaction volumes for performing PCR are preferably from 20 µl to 100 µl depending upon the preference of the user. However, the larger the reaction volume, the greater the amount of enzyme required and hence the higher the cost of performing the experiment.

The inventive primers and nucleic acids may be made by methods well known in the art, such as chemical synthesis. They may be synthesized manually or by machine. They may also be synthesized by recombinant methods using products incorporating viral and bacterial promoters available from Promega (Madison, Wis.).

The inventive primers include (but are not limited to) two oligonucleotides, the first of which has the following sequence (SEQ ID NO:1):

AACAAGCTTA ACAAAGAGAG ATTGTTT

This primer shall be identified in the present disclosure as VB21 and is identical to a sequence contained in the sense strand of the C. albicans gene for the large subunit of aminoadipate reductase. The sequence to which VB21 is complementary shall be identified herein as VB21'.

The second inventive primer (SEQ ID NO:2) has the following sequence:

AACAAGCTTC TGAAACCTCT AATCTT

This primer shall be identified in the present disclosure as VB22 and is identical to a sequence contained in the antisense strand of the C. albicans gene for the large subunit of aminoadipate reductase. The sequence to which VB22 is complementary shall be identified herein as VB22'.

Primers representing shortened or lengthened versions of VB21 and VB22 are also considered to be included in the present invention to the extent that they remain specific to the large subunit of the C. albicans gene for aminoadipate reductase. Furthermore, primers derived from the 526 base pair sequence that is amplified by means of the materials and methods described herein are also expected to be useful for identifying Candida albicans in a sample.

The primers of the present invention may be labeled, such as with radioactive isotopes, antigens, colorimetric compounds, fluorescent compounds, or other labelling agents known to those of ordinary skill in the art, to allow detection and quantification of DNA amplification. Furthermore, the nucleoside triphosphates used in the course of the amplification may also be labelled for detection using labels and detection procedures well known to those of ordinary skill in the art.

The present inventive methods employ inventive reagents for the detection of Candida albicans in a sample. The inventive reagents comprise the inventive primers and optionally comprise buffers, water, Tris-Cl, EDTA and/or additional components. Primers may also be supplied in lyophilized forms which may be reconstituted using solvents and methods known to those of ordinary skill in the art.

The present invention may be used to identify whether a subject is infected with Candida albicans. Because the large subunit of aminoadipate reductase is not known to be expressed by bacteria or any other non-fungal organisms, it provides a unique starting point for the materials and methods claimed herein. It is believed that the invention is appropriate for detecting C. albicans in biological samples and may detect other fungal pathogens in such samples.

Biological samples screenable via the present invention include samples obtained from healthy subjects or those with frank or occult disease. Samples appropriate for use in the current invention should be obtained from a site on or in the body where fungi do not constitute the normal flora. Blood is the preferred biological sample to be screened using the inventive materials and methods, as blood is presumed to be sterile and has no normal flora. The at-risk patients from which the samples are obtained include, but are not limited to mammals suffering from acquired immune deficiency syndrome, those under treatment with immunosuppressive drugs, postoperative patients and other immunocompromised patients. The samples may comprise tissues, including but not limited to solid tissues and swabbings from mucocutaneous membranes such as swabs from the oral cavity or the vagina, or fluids including but not limited to urine, blood, semen, cerebrospinal fluid or other bodily fluids. In a preferred embodiment, the sample is blood.

Nucleic acids screenable via the present invention include DNA (genomic DNA and cDNA). It is also possible that RNA may be screenable via the present invention in the event that the technique know in the art as RTPCR (reverse transcriptase PCR) is used. Other variations on the PCR technique known to those of ordinary skill in the art are also expected to be useful when conducted using the inventive primers. Therefore, use of such techniques are considered to be part of the present invention.

In the present invention, nucleic acids may be isolated from the biological samples or may remain embedded in such samples. In a preferred embodiment, the DNA is isolated from the biological samples. As used herein, "nucleic acids originating in a biological sample" encompasses DNAs either isolated from or contained in a biological sample.

In methods where nucleic acids are first isolated from the biological sample prior to screening, the nucleic acid should be obtained in a manner so as to maintain it in an essentially undegraded state. It will be understood by those with skill in the art that by "essentially undegraded" is meant that the nucleic acid samples will be of sufficient integrity that the genes in the sample will be detectable by the methods of this invention. Essentially undegraded nucleic acid is isolated by means well known to those with skill in the art. See, Sambrook et al., 1990, *Molecular Cloning: A Laboratory Manual* (Cold Spring Harbor Press: New York), hereby incorporated by reference.

Certain factors should be considered when implementing the present invention on a large scale, such as in a clinical laboratory. In general, technicians should take all reasonable steps to avoid contamination of samples to be screened by environmental materials. Such precautions are particularly important in connection with the present invention, because, as described below, a positive result in the PCR amplification may result from screening a sample containing a very small number of fungal cells. Thus, even small levels of contamination have the potential for causing false positive results, and for this reason technicians should be particularly careful to keep contamination to a minimum. Those of ordinary skill in the art are aware of the steps generally applied in maintaining aseptic technique; procedures consistent with such aseptic technique should be used in obtaining and maintaining the biological samples to be screened via the present invention.

In order to avoid possible contamination of clinical specimens with Candida genomic or plasmid DNA, it is desirable to store clinical specimens and materials used in connection with the present invention in a location physically separate from any general use, clinical or molecular biology laboratory. If possible, it is desirable to set aside a separate laboratory solely for the storage, handling and processing of clinical tissue samples to be screened via the present invention. The work surfaces of such laboratories should be easy to clean and disinfect. Preferably, specific equipment dedicated for use in connection with PCR should include refrigerators and freezers in which to store reagents and tissue samples as well as a microcentrifuge capable of handling up to 24 tubes simultaneously, a dry bath incubator (temperature adjustable), and pipette devices capable of handling volumes of 0.5 –10 μL, 10–50 μL, 40–200 μL and 100–1000 μL. Although autoclaved distilled water may be brought in from another laboratory, the room used for sample preparation and extraction should have its own stocks of reagent chemicals allowing extraction and storage buffers to be prepared in situ. The room should contain lab coats and gloves for the use of the workers; such materials should not leave the PCR laboratory. Disposable materials such as gloves, tubes and pipette tips should be ordered specifically for this lab and should not be stored in a general area or transferred from another laboratory. Unless a balance and pH meter may be accessed in a laboratory which is guaranteed to be free from contamination with fungi, it may be necessary to have this equipment in the PCR/extraction lab for the preparation of reagents.

Materials that should preferably be ordered specially for the PCR lab include plastic eppendorf style pipette tips (0.5–10, 10–200 and 100–1000 sizes) polypropylene microcentrifuge tubes, 0.5 and 1.5 ml sizes; polypropylene tube racks for above; disposable gloves; laboratory coats; ice buckets.

After they have been taken from a patient, clinical samples should be packaged in a manner to prevent contamination of the sample by fungi not originating in the sample. These samples should be delivered directly to the PCR/extraction lab where packaging may be removed. Upon receipt by the PCR/extraction lab, samples should be catalogued and divided into aliquots. Samples should be preserved at −20° C. if the need arises for an individual test to be repeated. A containment hood is not necessary in which to carry out the extractions, but may be desirable for maintaining sterile conditions. At a minimum, a specific bench should be designated for the work which should be regularly disinfected.

Controls for the extraction and test

Inside a freezer in the PCR/extraction lab, samples of tissue should be stored which are used as the positive and negative controls for the extraction. The negative control may be any blood sample from a healthy individual. Such blood samples may be possibly obtained from blood transfusion services, especially if the testing is being carried out by a hospital having blood transfusion services. Ideally, the positive control should be a blood or tissue sample from a patient known to be infected systemically with C. albicans. However, in practice it may not be practical to obtain such blood samples in large enough quantities to allow use as a positive control in repeated tests. In practice the use of a blood sample which has had C. albicans cells added to a given concentration as a positive control may be more feasible.

PCR Amplifications

PCRs may be set up in the PCR/extraction lab on a designated bench. It is often convenient to designate a buffer bench, which is a DNA-free area where lysis buffers, extraction buffers and PCR ingredients are mixed. Such materials are then transferred to other benches where the extractions will be carried out and samples or template DNAs are added to the PCRs. In order to standardize the PCR, it is common practice to make "master-mix" reactions rather than to set up reactions individually, i.e. if 20 PCRs are to be set up, a sample containing sufficient reaction buffer, primers, nucleotides and enzyme to complete all PCR reactions should be made up in one tube and then divided among 20 tubes whereupon the given DNA templates/sample aliquots should be added individually to each tube. (All chemical reagents identified herein were obtained from Fisher Scientific, Pittsburgh, Pa., unless otherwise noted).

Analysis of the PCRs

Having prepared the PCR reaction mixtures, for example, as described in this specification, the reactions may be run in a thermocycler, the location of which in the laboratory is not critical, however, the completed reactions should on no account be brought back into the PCR/extraction lab. After completion of the amplifications, the reactions may be analyzed by agarose gel electrophoresis. Electrophoresis may be carried out at any convenient location, however, the electrophoresis lab should be physically separate from the PCR/extraction lab and no materials should be transferred from the electrophoresis area into the PCR/extraction laboratory.

Amplification may be detected in a manner appropriate to the label (if any), such as by autoradiography or fluoroscopy. Unlabelled amplification products may be detected through ethidium bromide staining. Methods for detecting and quantifying the amplified DNA are well known to those of ordinary skill in the art. Although this specification refers to a specific extraction method for extraction of DNA from biological samples, any extraction method that results in isolated, essentially undegraded DNA of adequate yield may be used as long as the users adhere to the general conditions for the prevention of contamination.

One of ordinary skill in the art will be familiar with the techniques used to adjust the stringency of the reaction conditions and therefore minimize false positive and false negative amplifications. For example, use of a PCR optimization kit (for example, the PCR optimization kit available from Promega (Madison, Wis.)) may be desirable depending on the primer selected.

The present inventive reagents may contain a single inventive primer or multiple inventive primers. In addition, the inventive reagents may contain a variety of primers, each capable of causing amplification of fungal-specific oligonucleotides.

The PCR technique is described in *PCR Technology, Principles and Applications for DNA Amplification* (Erlich ed. 1989) and U.S. Pat. No. 4,683,202, the teachings of which are hereby incorporated by reference.

It is also possible that the PCR method known as "Touchdown" PCR would be useful in the amplifying DNA from fungi when the primers to be used are degenerate. This technique is described in R. H. Don, et al., 'Touchdown' PCR to circumvent spurious priming during gene amplification. Nucleic Acids Research, 19:4008 (1991) which is hereby incorporated by reference. Likewise, the technique of "hot start" PCR (Chou, Q. et al., *Nucleic Acids Research*, 20:1717 (1992)) may also be useful in the present invention.

The following examples further elucidate the present invention, but are not intended to limit it.

EXAMPLE 1

Primer Design

The lys1$^+$ gene of *Schizosaccharomyces pombe* which encodes the large subunit of aminoadipate reductase was sequenced. The putative amino acid sequence of this gene was compared to that of the LYS2 gene of *Saccharomyces cerevisiae* which encodes the same protein. Areas of conservation (both at the nucleotide and amino acid levels) were used to select possible PCR primer sites. A pair of primers were designed from two such conserved regions, VB17 (which (SEQ ID NO:3) is identical in sequence to a sequence found in the sense strand of this gene) and VB18 (which (SEQ ID NO:4) is identical in sequence to a sequence found in the antisense strand of this gene). The sequence of these primers is set forth below:

VB17 (sense): AACAAGCTTN ACNAAACGTG ATTGTCT    27

VB18 (antisense): AACAAGCTTC NGAANCCACG AATTTT    26 wherein the first and second N positions of VB17 (SEQ ID NO:3) represent G or A and wherein the first N of VB18 (SEQ ID NO:4) represents G or T and the second N of VB18 (SEQ ID NO:4) represents C or A.

Figure 4:
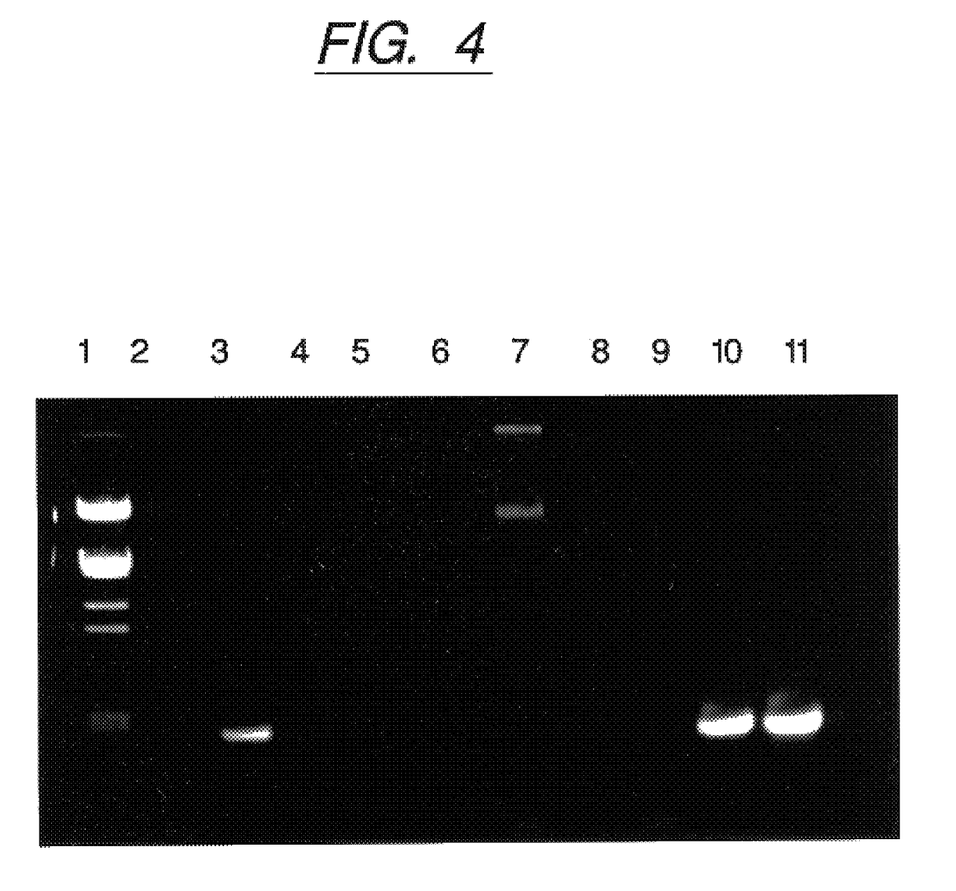
FIG. 4 is a photograph (taken under ultraviolet light) of a polyacrylamide gel following amplification using the primers VB17 and VB18 and eletrophoretic separation of the amplification products following PCR conducted on DNA extracted from a variety of organisms. The lanes, from left to right, contain the amplification product obtained from the following samples: (1) lambda PvuII size marker, (2) negative control (3) *C. albicans* (4) *E. coli*, (5) *B. megaterium*, (6) *S. coelicolor*, (7) *S. fradia*, (8) mouse, (9) human, (10) *S. cerevisiae*, and (11) *S. pombe*.

The primer pair was able to strongly amplify a product of approximately 500 base pairs from *S. cerevisiae* and *S. pombe* when used as amplification primers in PCR reactions (and electrophoresed) as described herein. A similar product was also amplified from *C. albicans* genomic DNA, although this amplification was weak (a photograph of the gel (stained with ethidium bromide) is set forth in FIG. 4).

The corresponding DNA sequence from *C. albicans* was obtained (Suvarna and Bhattacharjee, manuscript in preparation) and the primers were redesigned to be specific to *C. albicans* at these two sites. These two redesigned primers were named VB21 (SEQ ID NO:1) and VB22 (SEQ. ID NO:2), the sequences of which are:

VB 21: AACAAGCTTA ACAAAGAGAG ATTGTTT    27

VB22: AACAAGCTTC TGAAACCTCT AATCTT    26

These primers, when used in PCR procedures such as those described herein, will strongly amplify a 526 base pair oligonucleotide from gDNA originating in *C. albicans*. The sequence of the amplified oligonucleotide (SEQ. ID NO:5) is set forth in FIG. 2.

EXAMPLE 2

Synthesis of Primers

PCR primers were synthesized on a PerSeptive Biosystems (Campbridgem, Mass.) 8909 Expedite (TM) Nucleic Acids Synthesis System using the "DNA 0.2 μmol" program. The deoxynucleotides and HPLC-grade acetonitrile (the solvent used) were obtained from Perceptive Biosystems. The oligonucleotides were synthesized bound to 200 nmol size Controlled Pore Glass (CPG) columns. When the synthesis was complete, the contents of the column was decanted into a polypropylene screw-capped microcentrifuge tube. 1 ml of concentrated ammonium hydroxide (Fisher Scientific) was added and the mixture was incubated for a minimum of 10 hours at 55° C. to cleave the oligonucleotides from the glass bead matrix. The supernatant was decanted into a fresh tube and the ammonium hydroxide was removed by vacuum drying. The oligonucleotides were dissolved in 1 ml of sterile distilled water and the concentration was found by measuring the absorbance at 260 nm on a spectrophotometer.

EXAMPLE 3

Preparation of Biological Samples

As biological samples from patients were unavailable, biological samples containing known concentrations of *C. albicans* cells were prepared. Cultures of *C. albicans* were prepared and resuspended. Using a haemocytometer to determine cellular concentration, stock suspensions of *C. albicans* were prepared by serial dilution having the following cellular numbers in 0.1 ml of sterile water: $1\times10^5$, $1\times10^4$, $1\times10^3$, $1\times10^2$, $1\times10^1$, $1\times 10^0$, and 0. 0.1 ml of each of the stock suspensions was then added to 0.1 ml of human blood obtained from a male volunteer which had been collected in EDTA (Fisher Scientific) as an anticoagulant.

EXAMPLE 4

Preparation of DNA for Amplification

The blood/Candida mixtures thus prepared were then mixed with 0.1 ml of lysis buffer (10 mM Tris.Cl, pH 8 (Fisher Scientific); 320 mM sucrose (Fisher Scientific); 5 mM $MgCl_2$ (Fisher Scientific); 1% Triton X-100 (Fisher Scientific). The final compositions of the blood/Candida mixtures used in the present investigation are set forth below in Table I.

| No | C. albicans susp. (vol.) | # of C. albicans cells | Blood vol. | Lysis buff. vol. | Total Vo. |
|---|---|---|---|---|---|
| 1 | 0.1 ml | $1 \times 10_5$ | 0.1 ml | 0.1 ml | 0.3 ml |
| 2 | " | $1 \times 10_4$ | " | " | " |
| 3 | " | $1 \times 10_3$ | " | " | " |
| 4 | " | $1 \times 10_2$ | " | " | " |
| 5 | " | $1 \times 10_1$ | " | " | " |
| 6 | " | $1 \times 10_0$ | " | " | " |
| 7 | 0 ml | 0 | " | " | 0.2 ml |

The mixtures were left at room temperature for 10 minutes before being spun in an Eppendorf microcentrifuge at 14,000 rpm for 5 minutes. The supernatant was aspirated and the pellet was resuspended in another 0.5 ml of the lysis buffer described above. This was step was repeated; during the final wash in lysis buffer, 7 μl of 1 mg/ml DNase 1 (Sigma, St. Louis, Mo.) was added. This suspension was incubated at 37° C. for 30 min. followed by incubation at 100° C. for 10 min. The tubes were immediately cooled on ice. This suspension was centrifuged again for 5 minutes, the supernatant removed by aspiration and the pellet was resuspended in 0.1 ml of a solution containing 10 mM Tris.Cl pH 8.0 Fisher Scientific; 30 mM EDTA (Fisher Scientific) and 0.5% SDS (Fisher Scientific). The suspension thus prepared was incubated at 100° C. in a dry block incubator for 15 minutes after which 0.1 ml of 2.5M potassium acetate was added. The suspension was incubated on ice for 30 minutes after which precipitated debris was removed by centrifugation for 10 minutes at 14,000 rpm. The supernatant was transferred by pipetting to a fresh tube and 0.2 ml of isopropanol was added. The DNA was precipitated at −20° C. for 20 minutes and then centrifuged at 14,000 rpm for 10 minutes. The supernatant was aspirated and the pelleted DNA was resuspended in 70% ethanol centrifuged at 14,000 rpm and the supernatant was removed by aspiration. The pelleted DNA was then vacuum dried and resuspended in 50 μL $dH_2O$.

EXAMPLE 5

Amplification

3 μL aliquots of sample DNA prepared in Example 4 were used as templates in the PCR reactions described below. The primer reaction mixtures were prepared with the following concentrations of materials in a final reaction volume of 20

μL: dATP, dCTP, dGTP and dTTP at 0.2 mM each, 50 pmol of each of the primers prepared as described in Example 2, 2.5 mM MgCl2 and 2.5 units of Tag DNA polymerase (Promega, Wis.) in the magnesium free buffer supplied by the manufacturer (500 mM potassium chloride, 100 mM Tris-HCl pH 9.0, 1% Triton X-100). The reaction cycling conditions that were used are as follows: 94° C. for 3 min; 35 cycles of the following: 94° C. for one minute, 55° C. for 1 minute, 72° C. for 1 minute; 72° C. for 5 minutes to complete unfinished PCR products.

The volumes required of sterile water, buffer, magnesium chloride, nucleotides, PCR primers and Taq DNA polymerase were calcluated for the number of reactions to be carried out. The following reagents were combined per 100 μl of PCR mix:

10 μl 10× reaction buffer;
10 μl 25 mM magnesium chloride;
5 μl of forward PCR primer (100 ng/μl)
5 μl of reverse PCR primer (100 ng/μl)
1 μl 20 mM dNTPs;
0.4 μl of 5 units/μl Taq DNA polymerase
dH$_2$O to make 100 μl.

These were all combined in the above referenced order in one tube. This "master-mix" was then divided among the individual reaction tubes. Then the DNA templates were added to each tube, followed by enough mineral oil to cover the surface of the reaction mix. The PCRs were carried out using a Perkin Elmer DNA Thermal Cycler. The machine was programmed with three linked programs: (1) a denaturation program of 94° C. for 3 min.; (2) a program of 35 amplifications using 94° C. for 1 min, 55° C. for 1 min and 72° C. for 1 min; (3) a primer extension program of 72° C. for 5 min.

PCR was carried out on the biological samples as described above, on positive controls (3 μl of one of the biological sample templates added together with 10 ng of *C. albicans* genomic DNA) and on negative controls (samples prepared from biological tissue with no *C. albicans* cells added and PCRs with no DNA template added) and on genomic DNA derived from *Escherichia coli, Bacillus megaterium, S. pombe, S. cerevisiae*, mouse and human.

The completed PCRs were electrophoresed in 1% agarose gels containing ethidium bromide at 250 ng/ml in a running buffer of 40mM Tris base, 2 mM EDTA, and 20 mM sodium acetate at a constant voltage of 100V. Amplification of the 526 base pair oligonucleotide was detected through ethidium bromide staining and visualization.

Amplifications were obtained only from the genomic DNA of *C. albicans;* the amplified product was the 526 base pair oligonucleotide set forth in FIG. 1. The sequence of the amplified product was confirmed through enzymatic dideoxy sequencing (Promega's fmol DNA Cycle Sequencing System) to verify that this oligonucleotide corresponded to the nucleotide sequence of the *C. albicans* gene for the large subunit of the aminoadipate reductase gene. All of the genomic DNAs used had previously been tested for their competence as PCR templates by amplification with a pair of primers from a conserved ribosomal DNA target sequence.

EXAMPLE 6

Sensitivity of Primers VB21 and VB22 to *C. albicans* and Clinical Samples

Sensitivity to *C. albicans*

Figure 2:
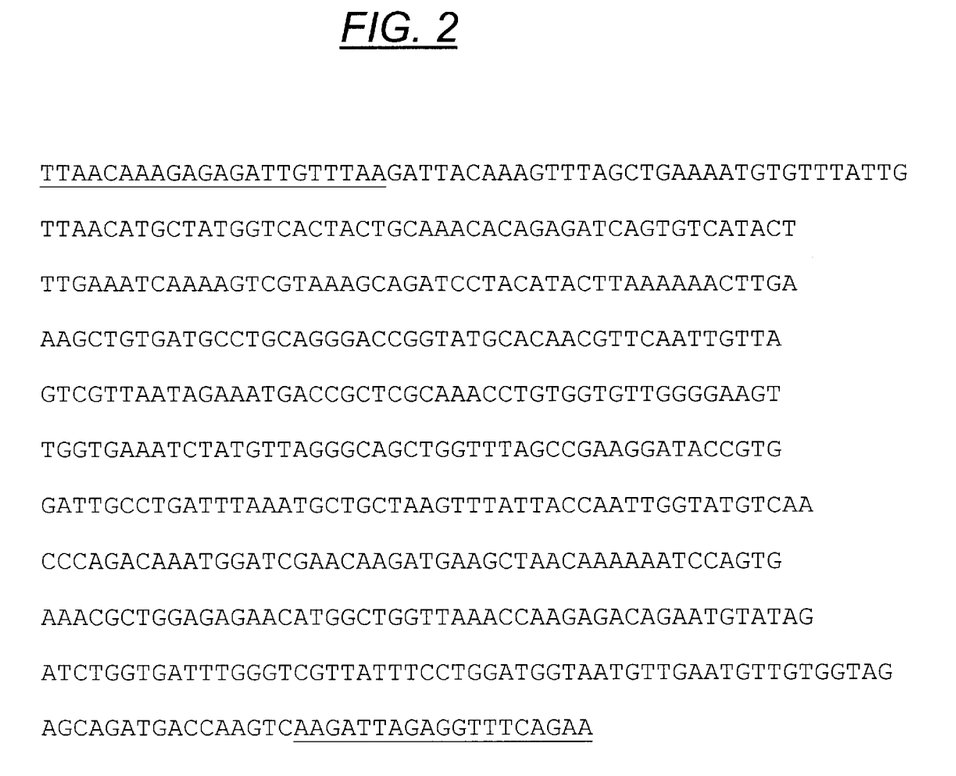
FIG. 2 provides the nucleotide sequence of the oligonucleotide that is amplified from *Candida albicans* using the primers of the present invention. The primers are underlined. The portion of the oligonucleotide sequenced is identified in bold.

The sensitivity of the primers VB21 and VB22 in amplifying the 526 base pair oligonucleotide identified in FIG. 2 was first investigated using genomic DNA extracted from *C. albicans* cells alone. DNA was extracted from $10^6$ cells and suspended in 50 μL of distilled water. A set of PCRs minus DNA template were prepared. 5 μl from the DNA extraction was added to the first PCR (providing this reaction with $10^5$ genome equivalents). This DNA template was serially diluted 1 in 10 and the prepared series of reaction tubes producing a range of diluted DNA templates from $10^5$ to $10^{-3}$ genome equivalents. After PCR amplification, the minimum amount of DNA which could provide visible amplification was $10^0$–$10^1$ genome equivalents. By this method, it was determined that the presently described and claimed method for screening a biological sample for the presence of *C. albicans* is useful when the original biological sample has a cellular concentration of *C. albicans* of 10–100 cells/ml.

Sensitivity of primers in screens of Clinical Samples

Figure 3:
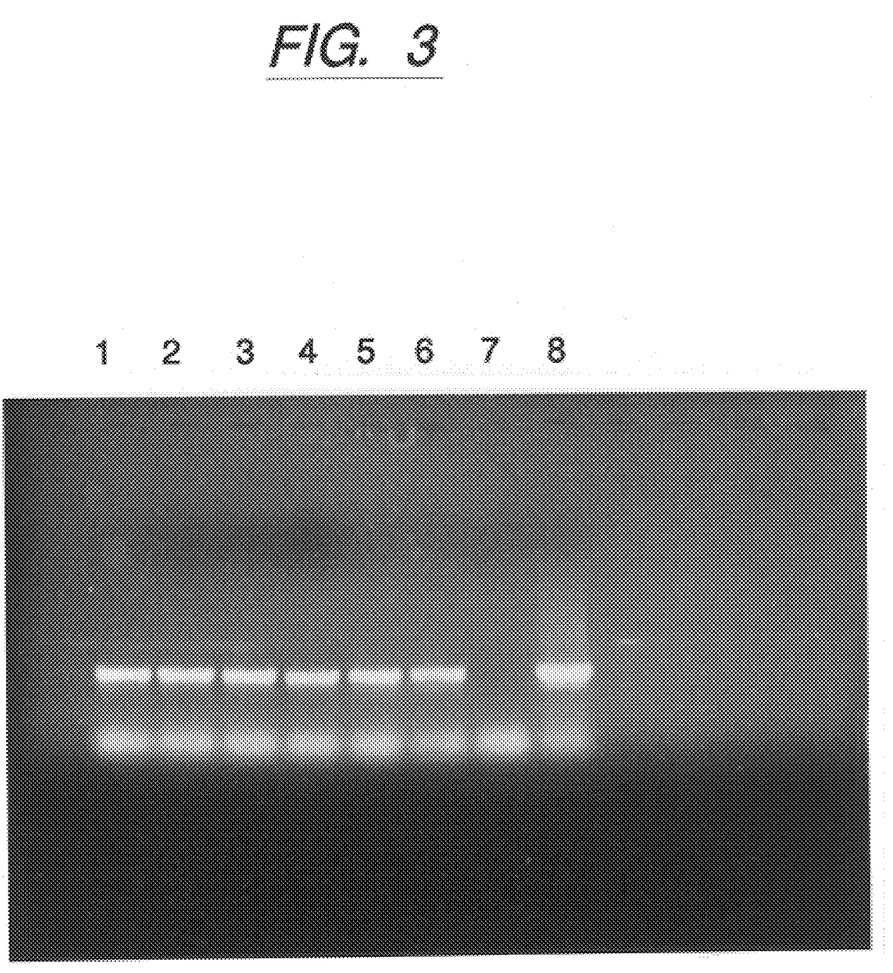
FIG. 3 is a photograph (taken under ultraviolet light) of a polyacrylamide gel following amplification using primers VB21 and VB22 and eletrophoretic separation of the amplification products following PCR conducted on biological samples having varying cellular number of *Candida albicans*. The lanes, from left to right, contain the amplification product obtained using the inventive primers to amplify DNA extracted from biological samples containing the following number of *Candida albicans* cells: (1) $10^6$, (2) $10^4$, (3) $10^3$, (4) $10^2$, (5) $10^1$, (6) $10^0$, (7) 0, (8) 0 cells+10 ng *C. albicans* genomic DNA.

The inventive primers were tested for their sensitivity in amplifying the 526 base pair oligonucleotide from a biological sample containing *C. albicans* as follows:

Suspensions of *C. albicans* were prepared having the following cellular numbers in 0.1 ml of sterile water: $1\times10^5$, $1\times10^4$, $1\times10^3$, $1\times10^2$, $1\times10^1$, $1\times10^0$, and 0. To each of these preparations, 100 μL of whole human blood (obtained from a male volunteer and collected in EDTA as an anticoagulant) or homogenized mouse kidney tissue in saline (prepared by homogenized the kidney of a freshly sacrificed mouse in 5 ml of sterile saline). DNA was extracted from these preparations as described in Example 4 and PCR was conducted as described in Example 5. A photograph of the electrophoretic gel (following ethidium bromide staining) corresponding to the PCRs conducted using spiked mouse kidney tissue as the biological sample is provided in FIG. 3.

Primers VB21 and VB22 were reproducibly able to amplify the 526 base pair oligonucleotide from biological samples having Candida concentrations of approximately 100 cells/ml.

In the both of the above described sensitivity determinations, strong bands were visible at the level of 100 cells/ml by ethidium bromide staining without any requirement for Southern transfer and hybridization to a radioactive probe.

EXAMPLE 7

Specificity of Primers VB21 and VB22

The primer pair VB21/VB22 were used in conducting PCR on gDNA obtained from the following fungal species: *S. pombe, S. cerevisiae, Aspergillus flavus, A. fumigatus, Coccidioides immitis, Histoplasma capsulatum, Pneumocysitis carinii, Candida tropicalis, C. krusei* and *C. glabrata*. Of these fungi, positive amplifications were obtained only from *C. tropicalis* and *C. krusei*.

We claim:

1. A nucleic acid having the nucleotide sequence (SEQ ID NO:1)

AACAAGCTTAACAAAGAGAGATTGTTT.

2. A nucleic acid having the nucleotide sequence (SEQ ID NO:2)

AACAAGCTTCTGAAACCTCTAATCTT.

3. A reagent comprising the nucleic acid of claim 1.
4. A reagent comprising the nucleic acid of claim 2.
5. A reagent comprising a first nucleic acid and a second nucleic acid, the first nucleic acid having the nucleotide sequence (SEQ ID NO:1)

AACAAGCTTAACAAAGAGAGATTGTTT.

and the second nucleic acid having the nucleotide sequence (SEQ ID NO:2)

AACAAGCTTCTGAAACCTCTAATCTT.

6. A nucleic acid amplification kit comprising the nucleic acid of claim 1.

7. A nucleic acid amplification kit comprising the nucleic acid of claim 2.

8. A nucleic acid amplification kit comprising the reagent of claim 5.

9. A method for amplifying a *Candida albicans* nucleic acid sequence having the sequence of SEQ ID NO: 5 from a nucleic acid sequence isolated from a biological sample obtained from a mammal, comprising hybridizing the isolated nucleic acid sequence with the nucleic acid of claim 1, and amplifying the isolated nucleic acid sequence (SEQ ID NO: 5).

10. A method for amplifying a *Candida albicans* nucleic acid sequence having the sequence of SEQ ID NO: 5 from a nucleic acid sequence isolated from a biological sample obtained from a mammal, comprising hybridizing the isolated nucleic acid sequence with the nucleic acid of claim 2, and amplifying the isolated nucleic acid sequence (SEQ ID NO: 5).

11. A method for amplifying a *Candida albicans* nucleic acid sequence having the sequence of SEQ ID NO: 5 from a nucleic acid sequence isolated from a biological sample obtained from a mammal, comprising hybridizing the isolated nucleic acid sequence with the first and second nucleic acid of claim 5 and amplifying the isolated nucleic acid sequence (SEQ ID NO: 5).

12. The method of claim 9 wherein the biological sample is blood.

13. The method of claim 10 wherein the biological sample is blood.

14. The method of claim 11 wherein the biological sample is blood.

15. The method of claim 9 wherein the mammal is a human.

16. The method of claim 10 wherein the mammal is a human.

17. The method of claim 11 wherein the mammal is a human.

18. A method of screening a biological sample for the presence of *Candida albicans* comprising the method of claim 9.

19. A method of screening a biological sample for the presence of *Candida albicans* comprising the method of claim 10.

20. A method of screening a biological sample for the presence of *Candida albicans* comprising the method of claim 11.

21. A method of amplifying a nucleic acid having the sequence (SEQ ID NO:5)

```
TTAACAAAGAGAGATTGTTTAAGATTACAAAGTTTAGCTG
    AAAATGTGTTTATTGTTAACATGCTATGGTCACTACTGC
    AAACACAGAGATCAGTGTCATACTTTGAAATCAAAAGT
    CGTAAAGCAGATCCTACATACTTAAAAAACTTGAAAGC
    TGTGATGCCTGCAGGGACCGGTATGCACAACGTTCAATT
    GTTAGTCGTTAATAGAAATGACCGCTCGCAAACCTGTGG
    TGTTGGGGAAGTTGGTGAAATCTATGTTAGGGCAGCTG
    TTTAGCCGAAGGATACCGTGGATTGCCTGATTTAAATGC
    TGCTAAGTTTATTACCAATTGGTATGTCAACCCAGACAA
    ATGGATCGAACAAGATGAAGCTAACAAAAAATCCAGT
    GAAACGCTGGAGAGAACATGGCTGGTTAAACCAAGAG
    ACAGAATGTATAGATCTGGTGATTTGGGTCGTTATTTCC
    TGGATGGTAATGTTGAATGTTGTGGTAGAGCAGATGAC
    CAAGTCAAGATTAGAGGTTTCAGAA
``` comprising conducting PCR using as a primer a nucleic acid according to claim 1.

22. A method of amplifying a nucleic acid having sequence (SEQ ID NO:5)

```
TTAACAAAGAGAGATTGTTTAAGATTACAAAGTTTAGCTG
    AAAATGTGTTTATTGTTAACATGCTATGGTCACTACTGC
    AAACACAGAGATCAGTGTCATACTTTGAAATCAAAAGT
    CGTAAAGCAGATCCTACATACTTAAAAAACTTGAAAGC
    TGTGATGCCTGCAGGGACCGGTATGCACAACGTTCAAT
    TGTTAGTCGTTAATAGAAATGACCGCTCGCAAACCTGT
    GGTGTTGGGGAAGTTGGTGAAATCTATGTTAGGGCAGC
    TGGTTTAGCCGAAGGATACCGTGGATTGCCTGATTTAAA
    TGCTGCTAAGTTTATTACCAATTGGTATGTCAACCCAGA
    CAAATGGATCGAACAAGATGAAGCTAACAAAAAATCC
    AGTGAAACGCTGGAGAGAACATGGCTGGTTAAACCA
    AGAGACAGAATGTATAGATCTGGTGATTTGGGTCGTTA
    TTTCCTGGATGGTAATGTTGAATGTTGTGGTAGAGCAG
    ATGACCAAGTCAAGATTAGAGGTTTCAGAA
``` comprising conducting PCR using as a primer a nucleic acids according to claim 2.

23. A nucleic acid having the nucleotide sequence (SEQ ID NO:5):

```
TTAACAAAGAGAGATTGTTTAAGATTACAAAGTTTAGCTG
    AAAATGTGTTTATTGTTAACATGCTATGGTCACTACTGC
    AAACACAGAGATCAGTGTCATACTTTGAAATCAAAAGT
    CGTAAAGCAGATCCTACATACTTAAAAAACTTGAAAGC
    TGTGATGCCTGCAGGGACCGGTATGCACAACGTTCAAT
    TGTTAGTCGTTAATAGAAATGACCGCTCGCAAACCTGT
    GGTGTTGGGGAAGTTGGTGAAATCTATGTTAGGGCAGC
    TGGTTTAGCCGAAGGATACCGTGGATTGCCTGATTTAAA
    TGCTGCTAAGTTTATTACCAATTGGTATGTCAACCCAGA
    CAAATGGATCGAACAAGATGAAGCTAACAAAAAATCC
    AGTGAAACGCTGGAGAGAACATGGCTGGTTAAACCAA
    GAGACAGAATGTATAGATCTGGTGATTTGGGTCGTTATT
    TCCTGGATGGTAATGTTGAATGTTGTGGTAGAGCAGAT
    GACCAAGTCAAGATTAGAGGTTTCAGAA.
```

24. A nucleic acid having a nucleotide sequence complementary to the nucleic acid sequence of claim 23.

* * * * *